United States Patent [19]

Haag et al.

[11] 4,157,338

[45] Jun. 5, 1979

[54] CONVERSION OF SYNTHESIS GAS TO HYDROCARBON MIXTURES

[75] Inventors: Werner O. Haag, Lawrenceville; Tracy J. Huang, Trenton, both of N.J.

[73] Assignee: Mobil Oil Corporation, New York, N.Y.

[21] Appl. No.: 883,970

[22] Filed: Mar. 6, 1978

Related U.S. Application Data

[63] Continuation of Ser. No. 729,242, Oct. 4, 1976, abandoned, which is a continuation of Ser. No. 566,161, Apr. 8, 1975, abandoned.

[51] Int. Cl.$^2$ .............................................. C07C 1/04
[52] U.S. Cl. ........................... 260/449 R; 260/449 M; 252/455 Z
[58] Field of Search ....... 260/449 R, 449 M, 449.6 R; 252/455 Z

[56] References Cited

U.S. PATENT DOCUMENTS

| | | | |
|---|---|---|---|
| 1,840,450 | 1/1932 | Jaeger et al. | 260/449.6 |
| 1,925,389 | 9/1933 | Jaeger | 260/449.6 |
| 2,754,314 | 7/1956 | McGrath | 260/449 |
| 3,013,990 | 12/1961 | Breck | 252/455 Z |
| 3,254,023 | 5/1966 | Miale et al. | 260/449 R |
| 3,702,886 | 11/1972 | Argawer et al. | 423/328 |
| 3,709,979 | 1/1973 | Chu | 252/455 Z |
| 3,871,993 | 3/1975 | Morrison et al. | 252/455 Z |
| 3,980,583 | 9/1976 | Mitchell et al. | 260/449 R |
| 4,086,262 | 10/1976 | Chang et al. | 260/449.6 R |

FOREIGN PATENT DOCUMENTS

| | | | |
|---|---|---|---|
| 1036837 | 8/1958 | Fed. Rep. of Germany | 260/449 R |
| 762705 | 12/1956 | United Kingdom | 260/449.6 |

OTHER PUBLICATIONS

Abdulahad et al., Brenn. Chemie, 25, No. 4, 1972, 187–188.

Storch et al., Fischer-Tropsch & Related Synthesis, John Wiley & Sons, New York, 1951, 428–435, 454–458.

*Primary Examiner*—Howard T. Mars
*Attorney, Agent, or Firm*—Charles A. Huggett; Carl D. Farnsworth

[57] ABSTRACT

A mixture of carbon monoxide and hydrogen is contacted with a mixture comprising an element selected from the group consisting of ruthenium, rhodium and osmium carbon monoxide reduction catalyst and a crystalline alumino-silicate providing a pore dimension greater than about 5 Angstroms and a constraint index in the range of 1 to 12 to produce hydrocarbon mixtures useful in forming gasoline boiling range products, aromatic rich hydrocarbons, and chemical intermediates.

5 Claims, 4 Drawing Figures

CONVERSION OF SYNTHESIS GAS TO HYDROCARBON MIXTURES

This application is a continuation of application Ser. No. 729,242, filed on Oct. 4, 1976, now abandoned, which in turn was a continuation of application Ser. No. 566,161, filed on Apr. 8, 1975, now abandoned.

BACKGROUND OF THE INVENTION

1. Field of the Invention

This invention is concerned with an improved process for converting synthesis gas, referred to as syngas, i.e., mixtures of gaseous carbon oxides with hydrogen or hydrogen donors, to form hydrocarbon mixtures. In one aspect, this invention is particularly concerned with a process for converting synthesis gas or syngas comprising carbon monoxide and hydrogen to hydrocarbon mixtures rich in aromatic hydrocarbons. In another aspect, this invention is concerned with a process for converting synthesis gas to hydrocarbon mixtures rich in $C_3+$ hydrocarbons and particularly $C_5+$ petroleum hydrocarbons. In still another aspect, this invention is concerned with providing novel catalyst composition for the conversion of synthesis gas to hydrocarbon mixtures.

2. Prior Art

Processes for the conversion of coal and other hydrocarbons such as natural gas to a gaseous mixture consisting essentially of hydrogen and carbon monoxide, or of hydrogen and carbon dioxide, or of hydrogen and carbon monoxide and carbon dioxide, are well known. Although various processes may be employed for the gasification, those of major importance depend either on the partial combustion of the fuel with an oxygen-containing gas or on the high temperature reaction of the fuel with steam, or on a combination of these two reactions. An excellent summary of the art of gas manufacture, including synthesis gas, from solid and liquid fuels, is given in Encyclopedia of Chemical Technology, Edited by Kirk-Othmer, Second Edition, Volume 10, pages 353–433, (1966), Interscience Publishers, New York, New York, the contents of which are herein incorporated by reference.

It is desirable to be able to effectively convert synthesis gas from any source such as from coal and natural gas, to highly valued hydrocarbons such as motor gasoline with high octane number, petrochemical feedstocks, liquefiable petroleum fuel gas, and aromatic hydrocarbons. It is well known that synthesis gas will undergo conversion to form reduction products of carbon monoxide, such as hydrocarbons, at from about 300° F. to about 850° F. under from about one to one thousand atmospheres pressure, over a fairly wide variety of catalysts. The Fischer-Tropsch process, for example, produces a range of liquid hydrocarbons, a portion of which have been used as low octane gasoline. The types of catalysts that have been studied for this and related processes include those based on metals or oxides of iron, cobalt, nickel, ruthenium, thorium, rhodium and osmium.

The wide range of catalysts and catalyst modifications disclosed in the art and an equally wide range of conversion conditions for the reduction of carbon monoxide by hydrogen provide considerable flexibility toward obtaining selected boiling-range products. Nonetheless, in spite of this flexibility, it has not proved possible to make such selection so as to produce liquid hydrocarbons in the gasoline boiling range which contain highly branched paraffins and substantial quantities of aromatic hydrocarbons, both of which are required for high quality gasoline, or to selectively produce aromatic hydrocarbons particularly rich in the benzene to xylenes range. A review of the status of this art is given in "Carbon Monoxide-Hydrogen Reactions", Encyclopedia of Chemical Technology, Edited by Kirk-Othmer, Second Edition, Volume 4, pp. 446–488, Interscience Publishers, New York, N.Y., the text of which is incorporated herein by reference.

In a book entitled "The Fischer-Tropsch and Related Synthesis" by Storch, Golumbic and Anderson, published by John Wiley and Sons, Inc., New York, it recites beginning page 309, "The use of ruthenium as a catalyst for the production of high melting wax from carbon monoxide and hydrogen was studied at the KWI for several years (1938–1941). The process is mostly of theoretical interest because of the high cost of ruthenium and the small commercial demand for the very high molecular weight paraffins produced by synthesis over ruthenium."

Further discussion of the investigation of ruthenium catalyst for the conversion of carbon monoxide and hydrogen is provided by H. Pichler in Advanced Catalysis, Vol. IV, 1952, beginning at page 289. Also an article published in I. & E.C. Product Research And Development, Vol. 4, No. 4, December 1955 beginning at page 265 by Karn, Schultz and Anderson entitled "Hydrogenation of Carbon Monoxide and Carbon Dioxide on Supported Ruthenium Catalysts At Moderate Pressure" emphasizes the unsuccessful results of the investigation for producing gasoline boiling range hydrocarbons. Only high molecular weight waxy materials were produced at pressures of 21.4 atmospheres and higher and methane was a primary product at 1 atmosphere pressure.

Recently it has been discovered that synthesis gas may be converted without intermediate formation of lower alcohols to higher hydrocarbons and particularly to $C_5+$ gasoline boiling range hydrocarbon products by catalytic contact of carbon monoxide and hydrogen synthesis gas with a ruthenium containing catalyst in admixture with a special type of crystalline zeolite catalyst of particularly selective conversion characteristics.

It is an object of the present invention to provide an improved process for converting synthesis gas to hydrocarbon mixtures that contain large quantities of highly desirable $C_5+$ carbon-hydrogen constituents. It is a further object of this invention to provide a ruthenium containing catalyst mixture suitable for converting a mixture of gaseous carbon oxides and hydrogen to a gasoline boiling range mixture of hydrocarbons. It is a further object of this invention to provide an improved method for converting synthesis gas under elevated pressure conditions to aromatic hydrocarbons. It is a further object of this invention to provide a method for converting synthesis gas to petrochemicals feedstocks, such as lower aromatics and olefins.

BRIEF SUMMARY OF THE INVENTION

It has now been discovered that valuable hydrocarbon mixtures may be produced by reacting synthesis gas, i.e., mixtures of hydrogen gas with gaseous carbon oxides, or the equivalents of such mixtures, in the presence of certain heterogeneous catalysts comprising intimate mixtures of at least two catalytically active components. The effective intimate mixtures, as will be more fully described hereinafter, are those in which the first component is selected from the class of inorganic substances that have catalytic activity for the reduction by hydrogen of carbon monoxide, and the second component is a crystalline aluminosilicate of particularly selective conversion characteristic. Depending on the choice of reactant components, the ratio employed and the particular reaction conditions selected, one may obtain substantial quantities of $C_5+$ liquid mixtures which are rich in branched paraffins and aromatic hydrocarbons and eminently suited for use in relatively high octane gasoline or as petrochemicals. Alternatively, one may select catalyst mixtures and operating conditions in a manner which will considerably vary the gaseous hydrocarbons formed as well as the aromatics formed boiling in the gasoline boiling range. The intimate catalyst mixtures of this invention which are distinctly novel, not only produce highly desirable products with good selectivity and yield but in many cases produce them with high conversion per pass under a variety of operating conditions. In accordance with this invention, it is surprising to find that when a preferred ZSM-5 crystalline aluminosilicate component is used in admixture with a selected amount of ruthenium that the catalytic activity and selectivity of the mixture is sustained for unusually long periods of time, the aromatic hydrocarbons are rich in toluene, xylenes, and $C_9$ aromatics. $C_{10}$ aromatics are substantially free of durene.

DETAILED DESCRIPTION AND PREFERRED EMBODIMENTS

Synthesis gas for use in this invention consists of a mixture of hydrogen gas with gaseous carbon oxides including carbon monoxide and carbon dioxide. By way of illustration, a typical purified synthesis gas will have the composition, on a water-free basis, in volume percentages, as follows: hydrogen, 51; carbon monoxide, 40; carbon dioxide, 4; methane, 1; and nitrogen, 4.

The synthesis gas may be prepared from fossil fuels by any of the known methods, including such in situ gasification processes as the underground partial combustion of coal and petroleum deposits. The term fossil fuels, as used herein, is intended to include anthracite and bituminous coal, lignite, crude petroleum, shale oil, oil from tar sands, natural gas, as well as fuels derived from simple physical separations or more profound transformations of these materials, including coked coal, petroleum coke, gas oil, residua from petroleum distillation, and two or more of any of the foregoing materials in combination. Other carbonaceous fuels such as peat, wood and cellulosic waste materials also may be used.

The raw synthesis gas produced from fossil fuels will contain various impurities such as particulates, sulfur compounds, and metal carbonyl compounds, and will be characterized by a hydrogen-to-carbon oxides ratio which will depend on the fossil fuel and the particular gasification technology utilized. In general, it is desirable for the efficiency of subsequent conversion steps to purify the raw synthesis gas by the removal of impurities. Techniques for such purification are known and are not part of this invention. It is preferred to adjust the hydrogen-to-carbon monoxide volume ratio to be within the range of from 0.2 to 6.0 and particularly in a ½ ratio upon contact with the catalyst. Should the purified synthesis gas be excessively rich in carbon oxides, it may be brought within the preferred range by the well known water-gas shift reaction. On the other hand, should the synthesis gas as prepared be rich in hydrogen, such as a 2/1 ratio, it may be adjusted into the preferred ½ range by the addition of recycle carbon monoxide since the products formed are approximately in a 2/1 ratio. Purified synthesis gas adjusted to contain the desired volume ratio of hydrogen-to-carbon monoxide or provided within the range of from 0.2 to 6.0 will be referred to as adjusted synthesis gas.

The heterogeneous catalyst mixture of this invention comprises at least two different catalyst components in which one component comprises a Group VIII precious metal such as, osmium, rhodium, ruthenium, and in which the other component is preferably an acidic crystalline alumino-silicate characterized by a pore dimension greater than about 5 Angstroms, a constraint index in the range of 1 to 12 and identified herein as a class of ZSM-5 crystalline zeolites. The catalyst mixture is prepared to provide generally a volume ratio of zeolite to metal greater than 20/1 and preferably it is about 50/1.

CATALYST

In accordance with this invention a specific catalyst consists of at least two components, the first being, for example, ruthenium and the second being a ZSM-5 type zeolite. The finished catalyst is in the form of either a loose mixture, pellet, or an extrudate.

The finished catalyst contains 0.05 to 10 percent (by weight) and preferably 0.2 to 1.5 percent (by weight) of a Group VIII metal.

Ruthenium can be incorporated in many ways. For example:
(1) Ruthenium dioxide is mixed or ground together with ZSM-5.
(2) Ruthenium is impregnated onto ZSM-5.
(3) Ruthenium is impregnated onto a separate support and then the supported ruthenium is mixed with ZSM-5. In this case, support can be refractory oxides, e.g., $SiO_2$, $Al_2O_3$, clays $TiO_2$, $ZrO_2$, etc., or other high surface area solids, e.g., activated carbon.

For impregnation employed in Methods (2) and (3), ruthenium salts or compounds, e.g., $RuCl_3\cdot3H_2O$, $Ru_3(CO)_{12}$, ruthenium acetylacetonate and potassium ruthenate, can be used. Aqueous or non-aqueous solvents, e.g., methanol, acetone, chloroform, hexane and benzene, can be used depending on the solubility of the ruthenium compound. After impregnation, the catalyst is vacuum dried at about 100° C. and then reduced at a temperature ranging from 150° to 600° C. with a reducing gas such as hydrogen or hydrogen containing gas such as $H_2/CO$ mixture. Reduction can be carried out under pressure. However, in case $H_2/CO$ mixture is used, low pressure such as 1 atm. is preferred. The time and temperature of reduction depends on the particular ruthenium compound used. For example, $RuO_2$ is easily reduced at 150° C. and atmospheric pressure of $H_2$, while $RuCl_3$ requires somewhat more severe conditions.

For the ZSM-5 type component, zeolites with a constraint index of 1–12, e.g., ZSM-5, ZSM-11, ZSM-21, ZSM-35 and ZSM-38 can be used in essentially hydrogen form. Binder such as silica or alumina can be employed in connection with pure zeolites.

While all catalysts prepared according to the above three methods give liquid hydrocarbons in the gasoline range, catalysts prepared from Method (2) or (3) are preferred especially at low ruthenium loading.

The crystalline aluminosilicates herein referred to also known as zeolites, constitute an unusual class of natural and synthetic minerals. They are characterized by having a rigid crystalline framework structure composed of an assembly of silicon and aluminum atoms, each surrounded by a tetrahedron of shared oxygen atoms, and a precisely defined pore structure. Exchangeable cations are present in the pores.

The preferred zeolite of this invention are selected from a recently discovered novel and special class of zeolites with unusual properties. These zeolites induce profound transformations of aliphatic hydrocarbons to aromatic hydrocarbons in commercially desirable yields and are generally highly effective in alkylation, isomerization, disproportionation and other reactions involving aromatic hydrocarbons. Although they have unusually low alumina contents, i.e., high silica to alumina ratios, they are very active even with silica to alumina ratios exceeding 30. This activity is surprising since catalytic activity of zeolites is generally attributed to framework aluminum atoms and cations associated with these aluminum atoms. These zeolites retain their crystallinity for long periods in spite of the presence of steam even at high temperatures which induce irreversible collapse of the crystal framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from, the intra-crystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred zeolites useful in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e., they exhibit "hydrophobic" properties. It is believed that this hydrophobic character is advantageous in the present invention.

The zeolites useful as catalysts in this invention freely sorb normal hexane and have a pore dimension greater than about 5 Angstroms. In addition, their structure must provide constrained access to some larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is substantially excluded and the zeolite is not of the desired type. Zeolites with windows of 10-membered rings are preferred, although excessive puckering or pore blockage may render these zeolites substantially ineffective. Zeolites with windows of twelve-membered rings do not generally appear to offer sufficient constraint to produce the advantageous conversions desired in the instant invention, although structures can be conceived, due to pore blockage or other cause, that may be operative.

Rather than attempt to judge from crystal structure whether or not a zeolite possesses the necessary constrained access, a simple determination of the "constraint index" may be made by continuously passing a mixture of equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1,000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of catalyst per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} (\text{fraction of n-hexane remaining})}{\log_{10} (\text{fraction of 3-methylpentane remaining})}$$

The constraint index approximates the ratio of the cracking rate constants for the two hydrocarbons. Catalysts suitable for the present invention are those which employ a zeolite having a constraint index from 1.0 to 12.0. Constraint Index (CI) values for some typical zeolites including some not within the scope of this invention are:

| CAS | C.I. |
| --- | --- |
| Erionite | 38 |
| ZSM-5 | 8.3 |
| ZSM-11 | 8.7 |
| ZSM-35 | 6.0 |
| TMA Offretite | 3.7 |
| ZSM-38 | 2.0 |
| ZSM-12 | 2 |
| Beta | 0.6 |
| ZSM-4 | 0.5 |
| Acid Mordenite | 0.5 |
| REY | 0.4 |
| Amorphous Silica-alumina | 0.6 |

The above-described Constraint Index is an important, and even critical, definition of those zeolites which are useful to catalyze the instant process. The very nature of this parameter and the recited technique by which it is determined, however, admit of the possibility that a given zeolite can be tested under somewhat different conditions and thereby have different constraint indexes. Constraint Index seems to vary somewhat with severity of operation (conversion). Therefore, it will be appreciated that it may be possible to so select test conditions to establish multiple constraint indexes for a particular given zeolite which may be both inside and outside the above defined range of 1 to 12.

Thus, it should be understood that the parameter and property "Constraint Index" as such value is used herein is an inclusive rather than an exclusive value. That is, a zeolite when tested by any combination of conditions within the testing definition set forth herein above to have a constraint index of 1 to 12 is intended to be included in the instant catalyst definition regardless that the same identical zeolite tested under other defined conditions may give a constraint index value outside of 1 to 12.

The class of zeolites defined herein is exemplified by ZSM-5, ZSM-11, ZSM-12, ZSM-21, and other similar materials. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

U.S. Application, Ser. No. 358,192, filed May 7, 1973, the entire contents of which are incorporated herein by reference, describes a zeolite composition, and a method of making such, designated as ZSM-21 which is useful in this invention. Recent evidence has been adduced which suggests that this composition may be composed of at least two (2) different zeolites designated ZSM-35 and ZSM-38, one or both of which are the effective material insofar as the catalysis of this invention is concerned. Either or all of these zeolites is considered to be within the scope of this invention.

The subject of ZSM-35 is described in U.S. Appln. Ser. No. 528,061 filed Nov. 29, 1974. The subject of ZSM-38 is described in U.S. Appln. Ser. No. 528,060 filed Nov. 29, 1974.

The specific zeolites described, when prepared in the presence of organic cations, are substantially catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this special type zeolite; however, the presence of these cations does appear to favor the formation of this special type of zeolite. More general, it is desirable to activate this type zeolite by base exchange with ammonium salts followed by calcination in air at about 1000° F. for from about 15 minutes to about 24 hours.

Natural zeolites may sometimes be converted to this type zeolite by various activation procedures and other treatments such as base exchange, steaming, alumina extraction and calcination, alone or in combinations. Natural minerals which may be so treated include ferrierite, brewsterite, stilbite, dachiardite, epistilbite, heulandite and clinoptilolite. The preferred crystalline aluminosilicates are ZSM-5, ZSM-11, ZSM-12 and ZSM-21, with ZSM-5 particularly preferred.

The zeolites used as catalysts in this invention may be in the hydrogen form or they may be base exchanged or impregnated to contain ammonium or a metal cation complement. It is desirable to calcine the zeolite after base exchange. The metal cations that may be present include any of the cations of the metals of Groups I through VIII of the periodic table. However, in the case of Group IA metals, the cation content should in no case be so large as to substantially eliminate the activity of the zeolite for the catalysis being employed in the instant invention. For example, a completely sodium exchanged H-ZSM-5 appears to be largely inactive for shape selective conversions required in the present invention.

In a preferred aspect of this invention, the zeolites useful as catalysts herein are selected as those having a crystal framework density, in the dry hydrogen form, of not substantially below about 1.6 grams per cubic centimeter. It has been found that zeolites which satisfy all three of these criteria are most desired. Therefore, the preferred catalysts of this invention are those comprising zeolite having a constraint index as defined above of about 1 to 12, a silica to alumina ratio of at least about 12 and a dried crystal density of not substantially less than about 1.6 grams per cubic centimeter. The dry density for known structures may be calculated from the number of silicon plus aluminum atoms per 1000 cubic Angstroms, as given, e.g. on page 19 of the article on Zeolite Structure by W. M. Meier. This paper, the entire contents of which are incorporated herein by reference, is included in "Proceedings of the Conference on Molecular Sieves, London, April, 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density of course must be associated with a relatively small amount of free space within the crystal, which might be expected to result in more stable structures. This free space, however, seems to be important as the locus of catalytic activity.

Crystal framework densities of some typical zeolites including some which are not within the purview of this invention are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

In the process of this invention, synthesis gas is contacted with the heterogeneous catalyst at a temperature of from about 300° F. to 1000° F., preferably from 450° F. to 850° F., at a pressure from 1 to 1000 atmospheres, preferably from 3 to 200 atmospheres, and at a volume hourly space velocity from about 100 to 50,000 volumes of gas, at standard temperature and pressure per volume of catalyst, or equivalent contact time if a fluidized bed is used. The heterogeneous catalyst may be contained as a fixed bed, a fluidized bed or a liquid slurry reactor may be used. The product stream containing hydrocarbons, unreacted gases and steam may be cooled and the hydrocarbons recovered by any of the techniques known in the art, which techniques do not constitute part of this invention. The recovered hydrocarbons may be further separated by distillation or other means to recover one or more products such as high octane gasoline, propane fuel, benzene, toluene, xylenes, or other aromatic hydrocarbons.

Tables 1 through 5 present the results obtained with the specific ruthenium-zeolite catalyst prepared as specified below.

DISCUSSION OF SPECIFIC EMBODIMENTS

Ruthenium dioxide has been used as a Fischer-Tropsch catalyst to convert synthesis gas into paraffin wax under high pressure (>100 atmos.) and low temperature (248°–428° F.). However, at higher temperature (572° F.), only methane is formed. Ruthenium-on-alumina has also been used for syngas conversion to produce gaseous, liquid and solid hydrocarbons; however, again, methane becomes the major product at temperatures higher than 482° F. No aromatics are produced using both catalysts. Recently it has been found that ruthenium, in combination with HZSM-5, produces aromatics-containing gasoline in good yield from syngas.

It has been found, for example, that with ruthenium/HZSM-5 catalyst, gasoline yield as well as quality can be substantially improved and methane formation can be greatly reduced by using proper optimum process conditions, such as pressure, temperature, space velocity and $H_2/CO$ ratio as herein defined.

EXPERIMENTAL

The following specific results supporting the concepts of this invention were obtained using 5% ruthenium/ZSM-5 as a catalyst, which was prepared by grinding together 20.0 grams of ZSM-5 and 1.39 grams of ruthenium dioxide, followed by pelleting and screening to a particle size of 30–60 mesh. The ruthenium dioxide containing ZSM-5 catalyst was then reduced in situ at 750 psig and 200° C. for 2 hours with hydrogen at a flow rate of 100 cc/min prior to syngas conversion.

In each run, 5.5 grams of catalyst was placed in a stainless steel reactor ($\frac{1}{2}''$ ID $\times 5\frac{1}{2}''$) which was equipped with a thermowell ($\frac{1}{8}''$ OD) in the center of the reactor. Syngas conversion was conducted in a fixed bed reactor in a downflow fashion. Syngas was introduced into the reactor from the top of the reactor at the desired pressure and flow rate and then the reactor was brought to the desired temperature. Gas and liquid products were separated and analyzed chromatographically.

The ZSM-5 component contained 65% of HZSM-5 and 35% of alumina binder. Syngas feed with various $H_2/CO$ ratios were employed.

Referring now to the graphs which are a plot of the data obtained in this investigation, the following observations are made from the data of Tables 1–5.

Table 1

| Effect of Pressure on Syngas Conversion over 5% Ru/HZSM-5 | | | | |
|---|---|---|---|---|
| 561° F., $H_2/CO$ = 2/1, WHSV = 0.32 | | | | |
| Run No. | 121-3 | 121-5 | 120-3 | 125-2 |
| Pressure, psig | 200 | 400 | 750 | 1100 |
| TOS, hrs. | 7-24 | 24-31 | 26-31 | 5-22 |
| Conversion, wt % | | | | |
| CO | 63 | 76 | 86 | 90 |
| $H_2$ | 77 | 89 | 96 | 98 |
| Total Product, wt % | | | | |
| Hydrocarbon | 29.8 | 35.2 | 35.5 | 37.4 |
| $H_2$ | 2.9 | 1.4 | 0.5 | 0.2 |
| CO | 32.6 | 20.8 | 11.8 | 8.8 |
| $CO_2$ | 1.8 | 3.1 | 3.6 | 3.8 |
| $H_2O$ | 32.9 | 39.5 | 48.6 | 49.8 |
| Hydrocarbon Composition, wt % | | | | |
| $C_1$ | 52.8 | 34.5 | 26.0 | 26.1 |
| $C_2°$ | 5.9 | 4.3 | 4.3 | 3.4 |
| $C_2=$ | — | — | — | — |
| $C_3°$ | 7.7 | 8.3 | 5.1 | 3.0 |
| $C_3=$ | — | — | 0.7 | 0.2 |
| i-$C_4$ | 10.3 | 12.1 | 5.6 | 3.5 |
| n-$C_4$ | 5.0 | 6.6 | 4.5 | 3.6 |
| $C_4=$ | — | — | 0.9 | — |
| i-$C_5$ | 6.3 | 6.8 | 5.4 | 4.1 |
| n-$C_5$ | 1.5 | 2.3 | 3.5 | 4.0 |
| $C_6+$ non-aromatics | 2.0 | 9.1 | 29.5 | 40.8 |
| Aromatics | 8.5 | 16.2 | 14.7 | 11.5 |
| $C_1 + C_2$ in Total H.C. | 58.7 | 38.8 | 30.3 | 29.5 |
| $C_5+$ in Total H.C. | 18.3 | 34.4 | 53.1 | 60.4 |
| Aromatics in $C_5+$ | 46.2 | 47.2 | 27.7 | 19.1 |
| Aromatics in $C_6+$ | 80.8 | 64.1 | 33.2 | 22.0 |
| Aromatics in Total H.C. | 8.5 | 16.2 | 14.7 | 11.5 |
| Hydrocarbon Selectivity | 98.0 | 97.0 | 97.4 | 97.0 |
| Octane No. (R+O) of Weathered Liquid Product | 104.2 | (94.5)* | (78.0)* | — |

*From a separate run under the same operating conditions.

Table 2

| Effect of Temperature on Syngas Conversion over 5% Ru/HZSM-5 | | | |
|---|---|---|---|
| 750 psig, WHSV = 0.32, $H_2/CO$ = 2/1 | | | |
| Run No. | 126-3 | 120-3 | 126-5 |
| Temp., °F. | 507 | 558 | 613 |
| TOS, hrs. | 7-24 | 26-31 | 30-47 |
| Conversion, wt % | | | |
| CO | 93 | 86 | 78 |
| $H_2$ | 98 | 96 | 97 |
| Total Product, wt % | | | |
| Hydrocarbon | 40.0 | 35.5 | 35.8 |
| $H_2$ | 0.2 | 0.5 | 0.4 |
| CO | 6.3 | 11.8 | 18.9 |
| $CO_2$ | 1.0 | 3.6 | 4.5 |
| $H_2O$ | 52.6 | 48.6 | 40.4 |
| Hydrocarbon Composition, wt % | | | |
| $C_1$ | 10.3 | 26.0 | 61.3 |

Table 2-continued

Effect of Temperature on
Syngas Conversion over 5% Ru/HZSM-5
750 psig, WHSV = 0.32, $H_2/CO$ = 2/1

| Run No. | 126-3 | 120-3 | 126-5 |
|---|---|---|---|
| $C_2°$ | 1.0 | 4.3 | 6.5 |
| $C_2=$ | — | — | — |
| $C_3°$ | 1.2 | 5.1 | 4.5 |
| $C_3=$ | 0.1 | 0.7 | — |
| i-$C_4$ | 1.9 | 5.6 | 5.3 |
| n-$C_4$ | 4.2 | 4.5 | 3.4 |
| $C_4=$ | 0.2 | 0.9 | — |
| i-$C_5$ | 3.1 | 5.4 | 3.9 |
| n-$C_5$ | 4.7 | 3.5 | 1.4 |
| $C_6+$ non-aromatics | 65.8 | 29.5 | 5.6 |
| Aromatics | 7.7 | 14.7 | 8.2 |
| $C_1 + C_2$ in Total H.C. | 11.3 | 30.3 | 67.8 |
| $C_5+$ in Total H.C. | 81.3 | 53.1 | 19.1 |
| Aromatics in $C_5+$ | 9.4 | 27.7 | 43.1 |
| Aromatics in $C_6+$ | 10.4 | 33.2 | 59.5 |
| Aromatics in Total H.C. | 7.7 | 14.7 | 8.2 |
| Hydrocarbon Selectivity | 99.2 | 97.4 | 95.8 |
| Bromine No. of Liq. Product | 90 | | |

Table 3

Effect of Space Velocity on Syngas Conversion over
5% Ru/HZSM-5
1100 psig, $H_2/CO$ = 2/1

| Run No. | 125-4 | 125-2 | 506-1 |
|---|---|---|---|
| WHSV | 0.12 | 0.32 | 0.95 |
| TOS, hrs. | 34–44 | 5–22 | 3–16 |
| Temp. °F. | 567 | 561 | 567 |
| Conversion, wt % | | | |
| CO | 91 | 90 | 93 |
| $H_2$ | 98 | 98 | 98 |
| Total Product, wt % | | | |
| Hydrocarbon | 37.0 | 37.4 | 34.9 |
| $H_2$ | 0.2 | 0.2 | 0.2 |
| CO | 7.6 | 8.8 | 5.8 |
| $CO_2$ | 9.2 | 3.8 | 0.9 |
| $H_2O$ | 46.0 | 49.8 | 58.1 |
| Hydrocarbon Composition, wt % | | | |
| $C_1$ | 34.4 | 26.1 | 13.4 |
| $C_2°$ | 5.1 | 3.4 | 1.6 |
| $C_2=$ | — | — | — |
| $C_3°$ | 5.0 | 3.0 | 1.8 |
| $C_3=$ | 0.1 | 0.2 | 0.1 |
| i-$C_4$ | 5.9 | 3.5 | 1.8 |
| n-$C_4$ | 4.1 | 3.6 | 2.6 |
| $C_4=$ | — | — | 0.1 |
| i-$C_5$ | 4.6 | 4.1 | 3.0 |
| n-$C_5$ | 3.3 | 4.0 | 3.7 |
| $C_6+$ non-aromatics | 23.7 | 40.8 | 58.7 |
| Aromatics | 14.0 | 11.5 | 13.3 |
| $C_1 + C_2$ in Total H.C. | 39.5 | 29.5 | 15.0 |
| $C_5+$ in Total H.C. | 45.6 | 60.4 | 78.7 |
| Aromatics in $C_5+$ | 30.7 | 19.1 | 16.9 |
| Aromatics in $C_6+$ | 37.3 | 22.0 | 18.5 |
| Aromatics in Total H.C. | 14.0 | 11.5 | 13.3 |
| Hydrocarbon Selectivity | 92.7 | 97.0 | 99.3 |

Table 4

Effect of $H_2/CO$ Ratio on Syngas Conversion over
5% Ru/HZSM-5
561° F., 400 psig, GHSV = 467

| Run No. | 122-5 | 122-6 | 122-8 |
|---|---|---|---|
| $H_2/CO$ mole ratio | 1/2 | 1/1 | 2/1 |
| TOS, hrs. | 20–28 | 28–44 | 27–68 |
| Conversion, wt. % | | | |
| CO | 20 | 38 | 78 |
| $H_2$ | 74 | 85 | 92 |
| Total Product, wt. % | | | |
| Hydrocarbon | 10.9 | 19.5 | 40.2 |
| $H_2$ | 0.9 | 1.0 | 1.0 |
| CO | 77.7 | 58.3 | 19.0 |
| $CO_2$ | 2.4 | 3.6 | 3.9 |
| $H_2O$ | 8.3 | 17.6 | 35.8 |
| Hydrocarbon Composition, wt % | | | |

Table 4-continued

Effect of $H_2/CO$ Ratio on Syngas Conversion over
5% Ru/HZSM-5
561° F., 400 psig, GHSV = 467

| Run No. | 122-5 | 122-6 | 122-8 |
|---|---|---|---|
| $C_1$ | 17.7 | 24.4 | 44.5 |
| $C_2°$ | 3.3 | 2.6 | 5.0 |
| $C_2-$ | — | — | — |
| $C_3°$ | 15.7 | 12.4 | 7.1 |
| $C_3=$ | 1.5 | — | — |
| i-$C_4$ | 20.5 | 19.9 | 10.5 |
| n-$C_4$ | 10.5 | 10.1 | 6.1 |
| $C_4=$ | — | — | — |
| i-$C_5$ | 8.9 | 9.9 | 6.1 |
| n-$C_5$ | 2.8 | 1.4 | 2.3 |
| $C_6+$ non-aromatics | 1.2 | 3.5 | 7.8 |
| Aromatics | 18.1 | 15.8 | 10.6 |
| $C_1 + C_2$ in Total H.C. | 21.0 | 27.0 | 49.5 |
| $C_5+$ in Total H.C. | 30.9 | 30.6 | 26.8 |
| Aromatics in $C_5+$ | 58.4 | 51.5 | 39.4 |
| Aromatics in $C_6+$ | 93.8 | 81.7 | 57.4 |
| Aromatics in Total H.C. | 18.1 | 15.8 | 10.6 |
| Hydrocarbon Selectivity | 92.0 | 93.5 | 96.3 |
| Octane No. (R+O) of Weathered Liquid Product | 105.4 | 103.3 | 94.5 |

Table 5

Boiling Range Distribution and Octane Number of
Weathered Liquid Hydrocarbon Products. (Operating
Conditions: 561° F., 400 psig, GHSV = 467, 5% Ru/HZSM-5.)

| Run No. | SG-122-5 | SG-122-6 | SG-122-8 |
|---|---|---|---|
| $H_2/CO$ | 1/2 | 1/1 | 2/1 |
| Boiling Range, °F., Liquid Product | | | |
| 1% OFF | 231 | 83 | 3 |
| 5 | 277 | 123 | 83 |
| 10 | 283 | 146 | 85 |
| 20 | 317 | 224 | 103 |
| 30 | 322 | 245 | 144 |
| 40 | 327 | 286 | 192 |
| 50 | 335 | 295 | 217 |
| 60 | 360 | 325 | 249 |
| 70 | 372 | 338 | 286 |
| 80 | 399 | 375 | 322 |
| 90 | 441 | 432 | 363 |
| 95 | 481 | 466 | 400 |
| 98 | 529 | 497 | 466 |
| 99 | 575 | 519 | 503 |
| Octane No. (R+O) | 105.4 | 103.3 | 94.5 |

PRESSURE

Figure 1:
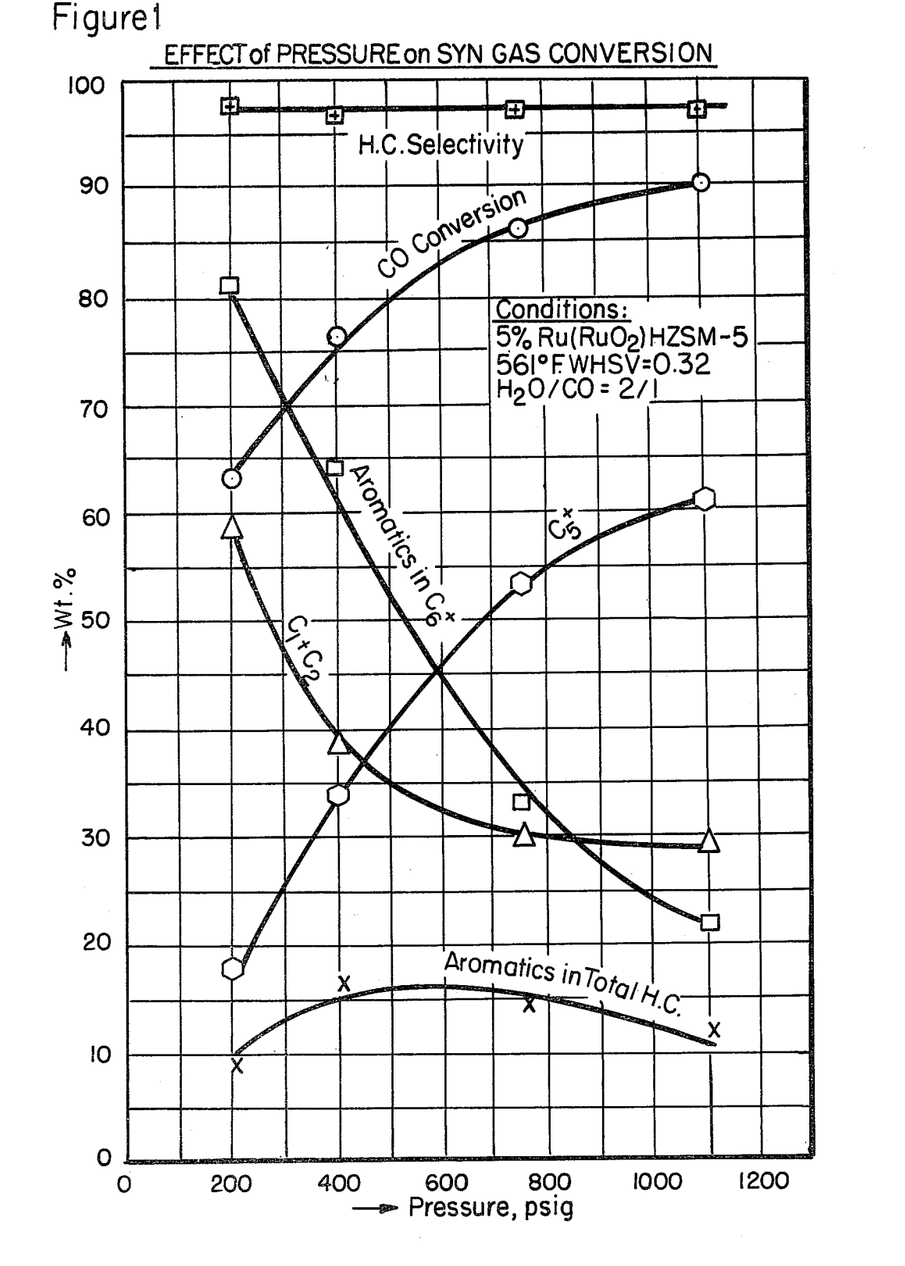
FIG. 1 is a plot of the data obtained showing the effect of pressure on the synthesis gas conversion in the presence of a particular ruthenium-crystalline zeolite conversion catalyst.

The effect of pressure on syngas conversion over Ru/ZSM-5 in the range of 200–1100 psig at 561° F., WHSV=0.32 and $H_2/CO$=2/1 is shown in FIG. 1 and Table 1. The selectivity of $C_5+$ in total hydrocarbon increased with increasing pressure while the aromatics in total hydrocarbon increased first and then decreased with increasing pressure, reaching an optimum production at near 400–800 psig. The $C_1+C_2$ gas make was substantially reduced by high pressure operation, for example 59% at 200 psig and 29% at 1100 psig. The fraction of $C_1+C_2$ represents mainly methane (80–90%) although grouped together.

Since low pressure gives poor $C_5+$ selectivity and very high pressure is costly, the desired intermediate pressure suitable for the Ru/ZSM-5 catalyzed syngas conversion process is in the range of about 200 to 2,000 psig, or preferably within the range of about 400 to 1,500 psig.

TEMPERATURE

Figure 2:
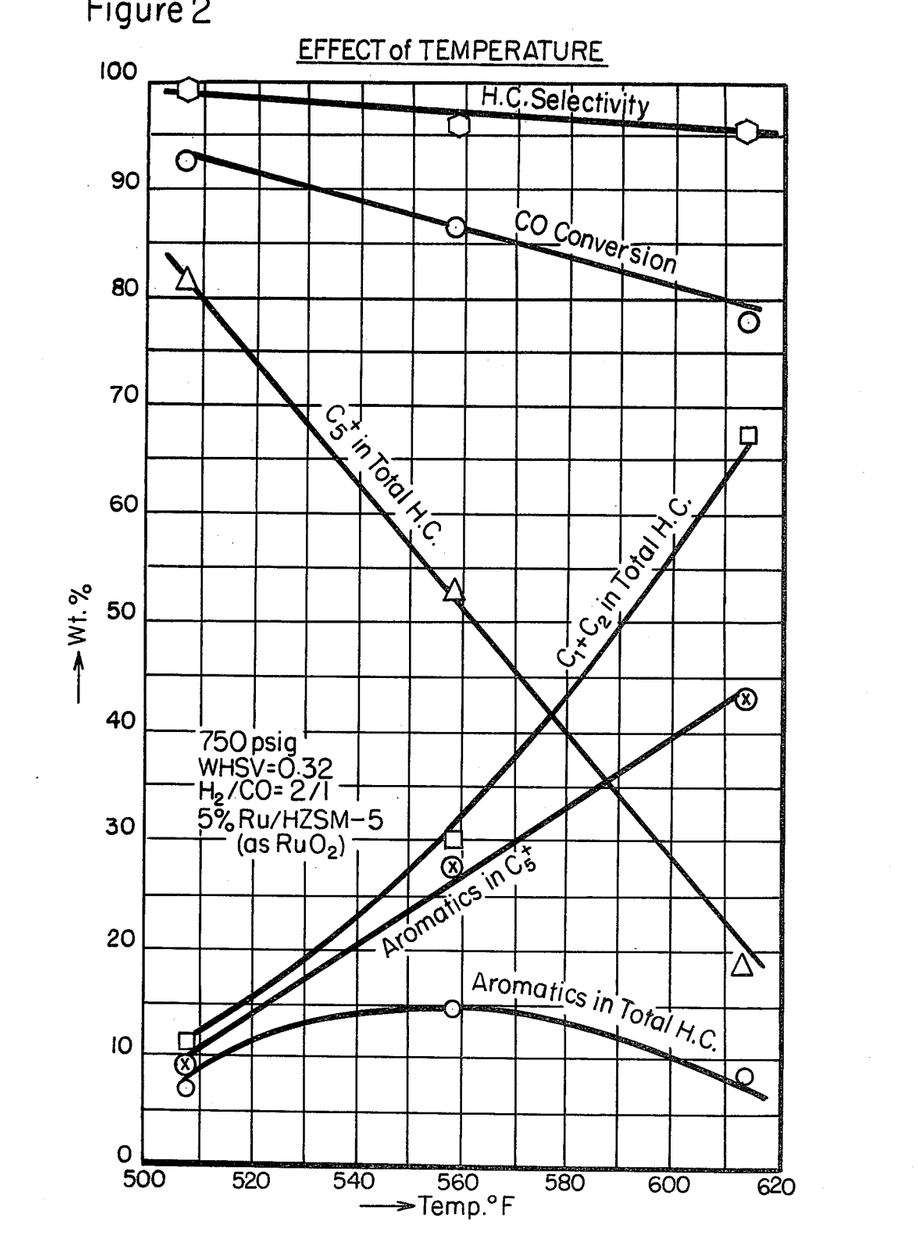
FIG. 2 is a plot of the data obtained showing the effect of temperature on the synthesis gas conversion in the presence of a particular ruthenium-crystalline zeolite conversion catalyst.

The effect of temperature on synthesis gas ($H_2/CO$) conversion in the range of 500°–620° F. at 750 psig, WHSV=0.32 and $H_2/CO=2/1$ is shown in FIG. 2 and Table 2. The two key features shown are the sharp increase in $C_5+$ and the sharp decrease in $C_1+C_2$ material shown as a function of decreasing temperature. For instance, $C_1+C_2$ was reduced from 68% at 613° F. to 11% at 507° F. The aromatics selectivity in $C_5+$ material increase with increasing temperature. It must be noted from Table 2 that the liquid hydrocarbon produced at 507° F. is quite olefinic (bromine number—90) although it contains less aromatics.

It is concluded from the data presented that the desired temperature for gasoline production from syngas conversion over a Ru/ZSM-5 catalyst mixture is in the range of about 470° F. to about 650° F., preferably within the range of about 490° to about 620° F. Since aromatic and olefinic gasoline are produced in this temperature range, the proper temperature for aromatic and olefinic gasoline production are more specifically described below:

For aromatic gasoline production, the desired temperature is in the range of about 530° to about 650° F., preferably within the range of about 540° to about 620° F., since at high temperatures methane make is increased. For predominantly olefinic gasoline production, the desired temperature is in the range of about 470° F. to 530° F., preferably within the range of about 490° F. to about 530° F., since at the lower temperatures the zeolite component tends to lose activity.

SPACE VELOCITY

Figure 3:
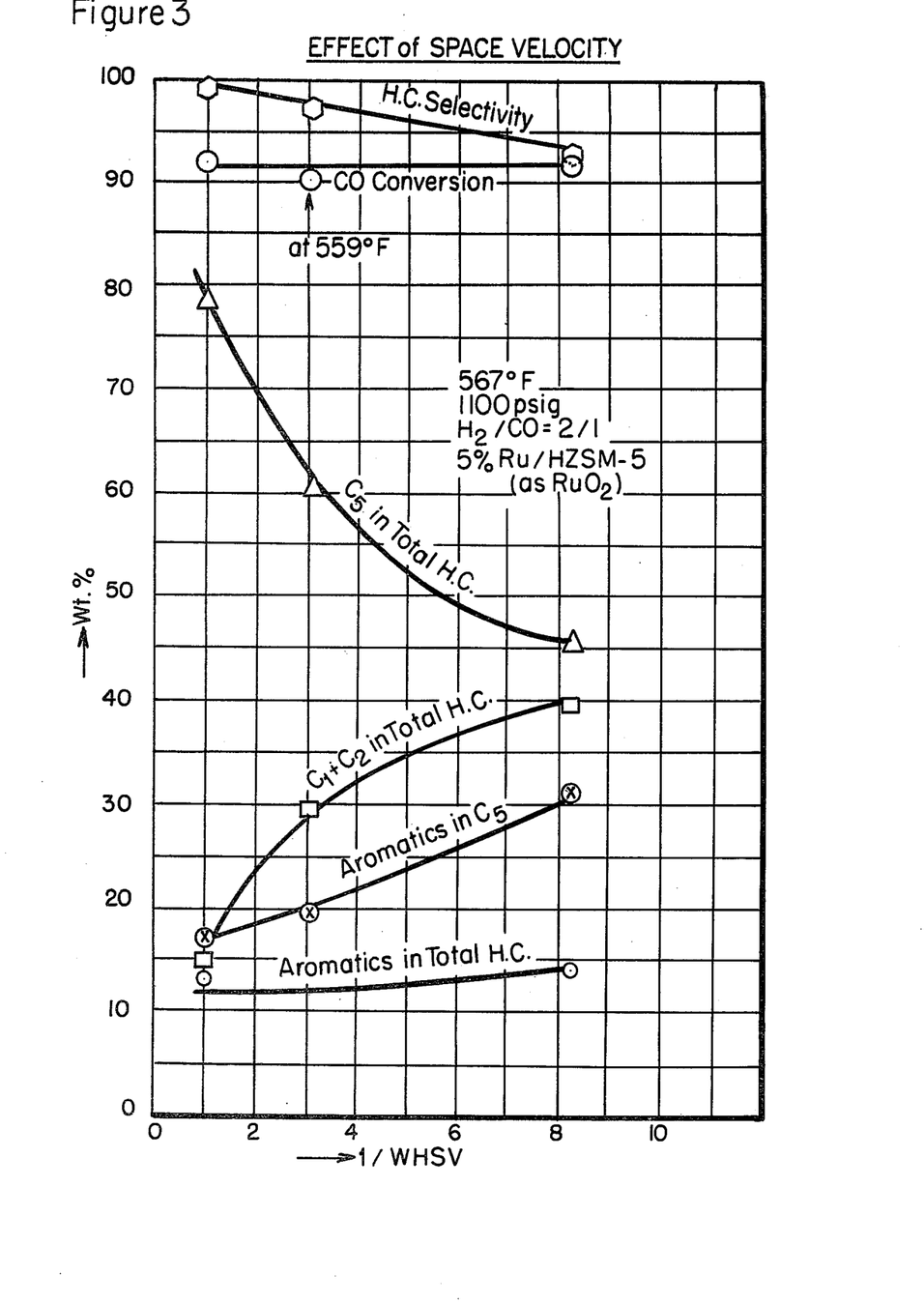
FIG. 3 is a plot of the data showing the effect of space velocity on the synthesis gas conversion in the presence of a particular ruthenium-crystalline zeolite conversion catalyst.

Syngas conversion may be carried out at weight hourly space velocity ranging from about 0.1 to about 10, preferably in the range of about 0.3 to about 3, as shown in FIG. 3. It is to be noted that one can use equivalent contact times in fluid bed operations. The graph of FIG. 3 is considered self-explanatory.

EFFECT OF $H_2/CO$ RATIO

Figure 4:
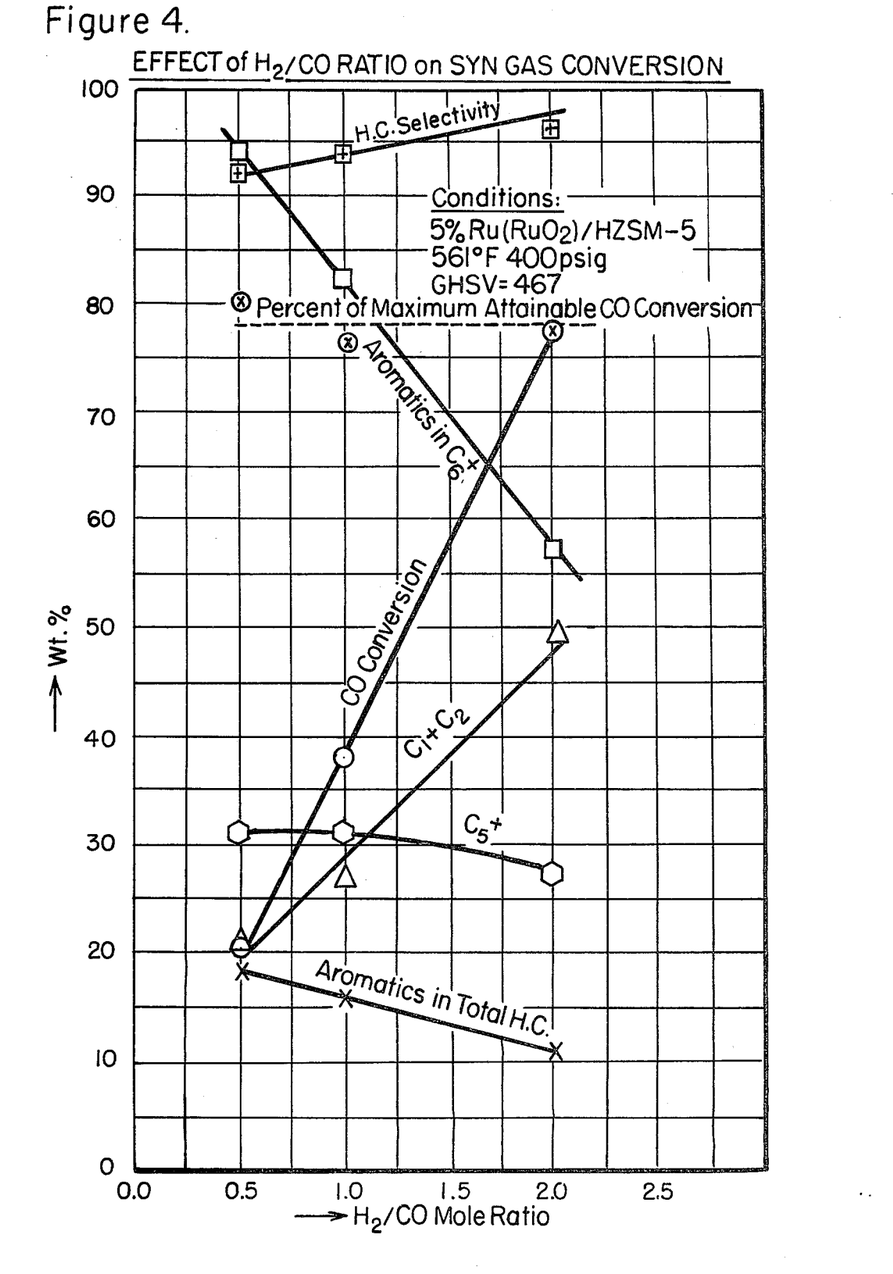
FIG. 4 is a plot of the data obtained showing the effect of $H_2/CO$ ratio on the synthesis gas conversion in the presence of a particular ruthenium-crystalline zeolite conversion catalyst.

Three different $H_2/CO$ ratios (½, 1/1, and 2/1) were used for the study of the effect of this ratio on syngas conversion which was at 561° F., 400 psig and GHSV=467. The detailed results are listed in Table 4. As shown in FIG. 4, the CO conversion increased (from 20 to 78%) with increasing $H_2/CO$ ratio. Since CO conversion is stoichiometrically limited by the amount of hydrogen available, the lower the $H_2/CO$ ratio, the lower the maximum attainable CO conversion. For example, with the $H_2/CO$ ratio of ½, the maximum attainable CO conversion, based on the stoichiometry of syngas conversion over Ru/HZSM-5 of $2H_2$:1 CO (2), would be 25%. Therefore, the 20% apparent CO conversion at the $H_2/CO$ ratio of ½ reflected 80% of the maximum attainable CO conversion. In the range of $H_2/CO$ ratio employed here, the possible CO conversion was all high, running at about 80% of the maximum attainable CO conversion, as represented by the dotted line in FIG. 4.

The $C_5+$ yield was rather insensitive to the $H_2/CO$ ratio in this range. However, the aromatics in $C_6+$ increased sharply with decreasing $H_2/CO$ ratio, reaching 94% at the $H_2/CO$ ratio of ½, and the total aromatics in hydrocarbon increased from 11% at 2/1 ratio to 18% at ½ ratio. More importantly, $C_1+C_2$ make decreased sharply with decreasing $H_2/CO$ ratio.

BOILING RANGE DISTRIBUTION AND OCTANE NUMBER

The boiling range distribution and octane number of some weathered liquid products obtained from syngas conversion over 5% Ru/HZSM-5 catalyst at 561° F., 400 psig and GHSV=467 using different $H_2/CO$ ratios are given in Table 5. The boiling range was shifted toward higher boiling point as the $H_2/CO$ ratio was decreased, although more aromatics and less methane were produced with lower $H_2/CO$ ratio. The weathered liquid hydrocarbon products gave the following octane numbers:

| $H_2/CO$ Ratio | 1/2 | 1/1 | 2/1 |
|---|---|---|---|
| Octane No. (R+O) | 105.4 | 103.3 | 94.5 |

The concepts and objectives of the present invention are further supported by the following examples.

EXAMPLE 1

1.39 grams of ruthenium dioxide and 20.0 grams of ZSM-5 containing 35% alumina binder was ground together and pelleted and screened to a particle size of 30–60 mesh. Then the catalyst was reduced at 750 psig and 200° C. for 2 hours with hydrogen at a flow rate of 100 cc/min. This catalyst contained 5% of ruthenium and is identified as Catalyst A.

EXAMPLE 2

1.25 grams of ruthenium trichloride trihydrate containing 40.39% ruthenium was dissolved in 18 ml of water and was added under vacuum to 10 grams of $NH_4ZSM-5$ containing 35% alumina binder (30–60 mesh). It was vacuum dried in a rotary evaporator at about 100° C. and further subjected to air calcination at 1000° F. for 2 hours in an oven. This resulted in a conversion of the ammonia form of ZSM-5 to the hydrogen form. The catalyst was reduced at 750° F. and 750 psig for 3 hours with flowing hydrogen at 60 cc/min. This impregnated catalyst contained 5% ruthenium and is identified as Catalyst B.

EXAMPLE 3

A 1% ruthenium/ZSM-5 catalyst was prepared using the procedure of Example 2, except that 20 grams of $NH_4ZSM-5$ with a 36 ml aqueous solution containing 0.5 gram of $RuCl_3.3H_2O$ was used. This catalyst is identified as Catalyst C.

EXAMPLE 4

A 10% ruthenium on γ-alumina catalyst was prepared by impregnating 10 grams of γ-alumina with a 35 ml aqueous solution containing 2.48 grams of ruthenium trichloride trihydrate (40.39% ruthenium). After drying in a rotary evaporator at about 100° C. and in a vacuum oven at 120° C. for 2 hours, the catalyst was reduced at 900° F. and 1 atm. for 12 hours with hydrogen flowing at 100 cc/min. This catalyst is identified as Catalyst D.

EXAMPLE 5

A 3% ruthenium on γ-alumina catalyst was prepared using the procedure of Example 4, except that 20 grams of γ-alumina with a 60 ml of aqueous solution containing 1.49 grams of $RuCl_3.3H_2O$ was used. This catalyst is identified as Catalyst E.

EXAMPLE 6

A 1% ruthenium on γ-alumina catalyst was prepared using the procedure of Example 4, except that 20 grams of γ-alumina with a 35 ml of aqueous solution containing 0.5 gram of $RuCl_3.3H_2O$ was used. This catalyst is identified as Catalyst F.

EXAMPLE 7

2.75 grams of Catalyst D (14–20 mesh) was mixed with 2.75 grams of quartz chips (14–20 mesh) and the mixture is identified as Catalyst G.

EXAMPLE 8

A mixed catalyst containing 5% ruthenium was prepared by mixing 2.75 grams of Catalyst D and 2.75 grams of HZSM-5 (35% alumina binder), both in 14–20 mesh. This mixed catalyst is identified as Catalyst H.

EXAMPLE 9

A mixed catalyst containing 1.5% ruthenium was prepared by mixing 2.75 grams of Catalyst E and 2.75 grams of pure HZSM, both in 14–20 mesh. This is identified as Catalyst I.

EXAMPLE 10

2.75 grams of Catalyst F (14–20 mesh) was mixed with 2.75 grams of quartz chips (14–20 mesh), and the mixture is identified as Catalyst J.

EXAMPLE 11

A mixed catalyst containing 0.5% ruthenium was prepared by mixing 2.75 grams of Catalyst F and 2.75 grams of pure HZSM-5 both in 14–20 mesh. This is identified as Catalyst K.

EXAMPLE 12

A mixed catalyst containing 0.5% ruthenium was prepared by mixing 2.75 grams of Catalyst F and 2.75 grams of mordenite ($SiO_2/Al_2O_3$=93), both in 14–20 mesh. This is identified as Catalyst L.

DATA ON CATALYTIC PERFORMANCE (EXP. 13–21)

Catalysts prepared in the above examples were tested for synthesis gas conversion conducted at 750 psig. ~560° F., WHSV=0.32 and $H_2/CO$=2/1 in a fixed bed stainless steel reactor in a downflow fashion. 5.5 grams of catalyst was used in each run. Gas and liquid products were separated and analyzed chromatographically. The results are shown in Table 6. The beneficial effect of HZSM-5 for aromatic gasoline production is clearly demonstrated in the comparison between Catalyst G (5% Ru/γ-$Al_2O_3$/quartz chips and Catalyst H (5% Ru/γ-$Al_2O_3$/HZSM-5) and the comparison among Catalyst J (0.5% Ru/γ-$Al_2O_3$/quartz chips, Catalyst K (0.5% Ru/γ-$Al_2O_3$/HZSM-5) and Catalyst L (0.5% Ru/γ-$Al_2O_3$/Mordenite), as reflected by the high aromatics content in $C_5+$ gasoline and the lower boiling range of liquid product in the cases where HZSM-5 is employed. Furthermore, regardless of method of catalyst preparation, ruthenium, in combination with HZSM-5, produced aromatic gasoline in good yield.

As can be seen from a comparison of experiment 19 (Ru catalyst) and 21 (Ru+mordenite), the mordenite containing catalyst differs very little from Ru alone; it makes no aromatics, the liquid product has a much higher distillation end point and is thus not in the gasoline boiling range as is the Ru/ZSM-5 produced liquid (Experiment 20).

Table 6

| | | | | | |
|---|---|---|---|---|---|
| | Synthesis Gas Conversion over Ruthenium/HZSM-5 Catalysts at 750 psig, WHSV = 0.32 and $H_2/CO$ = 2/1 | | | | |
| Experimental No. | 13 | 14 | 15 | 16 | 17 |
| Catalyst | A | B | C | G | H |
| Catalyst Description | 5% Ru/ZSM-5 "Phys. Mix." ($RuO_2$) | 5% Ru/ZSZ-5 "Impreg." | 1% Ru/ZSM-5 "Impreg." | 5%Ru/$Al_2O_3$/ Quartz Chips "Mixed" | 5% Ru/$Al_2O_3$/ ZSM-5 "Mixed" |
| Temp. (Ave.), °F. | 558 | 586 | 580 | 560 | 565 |
| Conversion, Wt % | | | | | |
| CO | 86 | 83 | 79 | 100 | 100 |
| $H_2$ | 96 | 88 | 85 | 100 | 99 |
| Reactor Effluent, Wt % | | | | | |
| Hydrocarbons | 36 | 38 | 32 | 35 | 40 |
| $H_2$ | 0 | 1 | 2 | 0 | 0 |
| CO | 12 | 15 | 18 | 0 | 0 |
| $CO_2$ | 4 | 2 | 3 | 37 | 20 |
| $H_2O$ | 48 | 44 | 45 | 28 | 40 |
| Hydrocarbon Composition, Wt % | | | | | |
| $C_1+C_2$ | 30 | 38 | 20 | 99 | 43 |
| $C_3+C_4$ | 17 | 16 | 29 | 1 | 14 |
| $C_5+$ | 53 | 46 | 51 | 0 | 43 |
| Aromatics in $C_5+$, Wt. % | 28 | 25 | 27 | 0 | 24 |
| Boiling Range of Liquid Product, °F. | | | | | |
| 90% Overhead Cut | 354 | — | — | — | — |
| 95% Overhead Cut | 395 | — | — | — | — |

| | 18 | 19 | 20 | 21 |
|---|---|---|---|---|
| Experiment No. | I | J | K | L |
| Catalyst | 1.5% Ru/ $Al_2O_3$/ZSM-5 | 0.5% Ru/$Al_2O_3$/ Quartz Chips | 0.5% Ru/ $Al_2O_3$/ZSM-5 | 0.5% Ru/ $Al_2O_3$/ Mordenite |
| Catalyst Description | "Mixed" | "Mixed" | "Mixed" | "Mixed" |
| Temp. (Ave.), °F. | 561 | 561 | 561 | 561 |
| Conversion, Wt. % | | | | |
| CO | 100 | 88 | 99 | 93 |

Table 6-continued

Synthesis Gas Conversion over Ruthenium/HZSM-5
Catalysts at 750 psig, WHSV = 0.32 and $H_2/CO$ = 2/1

| | | | | |
|---|---|---|---|---|
| $H_2$ | 99 | 97 | 97 | 96 |
| Reactor Effluent, Wt. % | | | | |
| Hydrocarbons | 39 | 37 | 38 | 36 |
| $H_2$ | 0 | 0 | 0 | 1 |
| CO | 0 | 11 | 1 | 6 |
| $CO_2$ | 17 | 6 | 12 | 8 |
| $H_2O$ | 44 | 46 | 49 | 49 |
| Hydrocarbon Composition, Wt. % | | | | |
| $C_1+C_2$ | 40 | 33 | 25 | 29 |
| $C_3+C_4$ | 12 | 8 | 9 | 7 |
| $C_5+$ | 48 | 59 | 66 | 63 |
| Aromatics in $C_5+$, Wt % | 32 | 0 | 34 | 0 |
| Boiling Range of Liquid Product, °F. | | | | |
| 90% Overhead Cut | 346 | 611 | 403 | 528 |
| 95% Overhead Cut | 367 | 711 | 440 | 611 |

In the conversion operation of this invention, it has been found advantageous to effect start-up of the operation by preheating the catalytic mixture to a temperature promoting effective conversion with the zeolite component of materials formed by the ruthenium component of the mixture. Thus it has been found desirable to initiate preheating of the catalyst with relatively inert gases, hydrogen alone, carbon oxides alone or mixtures of carbon monoxide and hydrogen not particularly effective in deactivating the catalyst mixture with waxy components before attaining desired operating conditions. In a particular aspect it is preferred to preheat the catalyst to a temperature of at least about 450° F. before contacting the catalyst with a synthesis gas mixture in a $H_2/CO$ ratio promoting the formation of desired liquid products. Thus it is contemplated effecting start-up in a reducing atmosphere until the catalyst attains a predetermined desired temperature and then the ratio of $H_2/CO$ is adjusted by the addition of CO to an inflowing hydrogen rich gas stream.

CARBON MONOXIDE RECYCLE

Synthesis gas conversion over ruthenium/ZSM-5 type catalysts is found to occur approximately according to the following stoichiometry:

$$2H_2 + 1\ CO \rightarrow [CH_2] + H_2O$$

where [$CH_2$] represents the overall composition of the hydrocarbons produced. This stoichiometry requires the use of a synthesis gas with an approximate molar ratio of $H_2/CO=2/1$ for best utilization of both reactants. It is now discovered however that a synthesis gas feed with a $H_2/CO$ ratio lower than 2 (for example $H_2/CO=1:2$) gives a more desirable product distribution particularly a larger $C_3+$ yield, a gasoline fraction richer in aromatics and less dry gas (methane and ethane). Such a more advantageous hydrogen-poor synthesis gas is however difficult to produce economically, and above all, results in low carbon monoxide conversion due to the stoichiometrical constraints.

It is proposed therefore to carry out the synthesis gas conversion by a novel method in which a net feed of $H_2$ and CO in a molar ratio of about 2 is used but which incorporates the product selectivity advantage of a feed containing $H_2/CO<2$, e.g., 0.1–1. This is accomplished by separating light gases containing excess carbon monoxide from the reactor product effluent and recycling these separated gases together with fresh feed to the catalytic syngas conversion reactor. This kind of operation not only gives improved product selectivity but aids in heat removal from the highly exothermic reaction; it gives a lower temperature increase in adiabatic reactors or a better temperature control in isothermal reactors by avoiding the formation of local hot spots.

For a given fresh feed composition (A) the ratio of $H_2/CO$ entering a reactor (C) can be varied as desired by adjusting the recycle ratio, i.e., the ratio of a recycle stream B to fresh feed stream A as shown by the following table that are obtained for 100% $H_2$ conversion and a $H_2/CO$ ratio in A of 2:1. It is seen that a recycle ratio of 1, 3 and 6.33, leads to a $H_2/CO$ ratio at the reactor inlet of 1:2, 1:5 and 1:10, respectively.

| Recycle Ratio | | Liters/Hour | | | |
|---|---|---|---|---|---|
| Stream B/A | | A | B | C | D |
| 1 | $H_2$ | 100 | — | 100 | 100 |
| | CO | 50 | 150 | 200 | 50 |
| | $H_2/CO$ | 2:1 | | 1:2 | |
| 3 | $H_2$ | 100 | — | 100 | 100 |
| | CO | 50 | 450 | 500 | 50 |
| | $H_2/CO$ | 2:1 | | 1:5 | |
| 6.33 | $H_2$ | 100 | — | 100 | 100 |
| | CO | 50 | 950 | 1000 | 50 |
| | $H_2/CO$ | 2:1 | | 1:10 | |

The reactor effluent obtained by the method and concepts of this invention is cooled and a hydrocarbon product is separated in a pressure separator from the excess carbon monoxide which is then recycled. Usually the CO recycle stream B will contain small amounts of light gases, particularly methane and some ethane. In order to prevent their buildup to unacceptably high levels in the recycle stream, a small slip stream is withdrawn; carbon monoxide makeup can be added if needed.

EXAMPLE 13

Ruthenium dioxide has been used as a Fischer-Tropsch catalyst to convert synthesis gas into paraffin wax under high pressure and low temperature (248–428° F.). However, at higher temperature (572° F.), only methane is formed. Ruthenium-on-aluminum has also been used for synthesis conversion to produce gaseous, liquid and solid hydrocarbons; however, again, methane becomes the major product at temperatures higher than 482° F. No aromatics are produced using these catalysts. Now, it has been found that ruthenium, in combination with HZSM-5, produces aromatics-containing gasoline in high yield from synthesis gas over a wide temperature range.

EXAMPLE A

A 5% ruthenium on ZSM-5 catalyst was prepared by vacuum impregnating 10 g. of $NH_4$-ZSM-5 with a 18 ml. aqueous solution containing 1.25 g. $RuCl_3.3H_2O$. After drying in vacuum the catalyst was air calcined in an oven at 1000° F. for two hours. This resulted in a conversion of the ammonium form of ZSM-5 to the hydrogen form.

EXAMPLE B

A 1% Ru/ZSM-5 catalyst was prepared using the procedure of Example A, except that 20 g. of $NH_4$-ZSM-5 with a 36 ml. aqueous solution containing 0.5 g. of $RuCl_3.3H_2O$ was used.

EXAMPLE C

The conversion of synthesis gas ($H_2$/CO) was carried out in a fixed-bed continuous flow reactor. The stainless steel reactor was charged with 5.5 g. of the 5% Ru/ZSM-5 catalyst prepared in Example A; the catalyst was prereduced with flowing hydrogen at 750° F. and a pressure of 750 psig for three hours.

The conversion of synthesis gas ($H_2$/CO) was carried out at 750 psig.~580° F. WHSV=0.32 and $H_2$/CO=2/1. The results and the detailed hydrocarbon distribution are given in Table 13 below. High conversion with good selectivity to liquid ($C_5+$) products was obtained. The liquid product contained 25% aromatics and had octane numbers R+0=77 and R+3=92.

EXAMPLE D

Syngas conversion was carried out under essentially the same conditions as in Example C except that 5.5 g. of 1% Ru/ZSM-5 prepared in Example B was used. The results are listed in Table 13 below. High conversion to hydrocarbons rich in $C_2+$ and containing 13.8% aromatics was obtained.

Table 13

Synthesis Gas Conversion over Ruthenium/HZSM-5 Catalyst at 750 psig~580° F. WHSV = 0.32 and $H_2$/CO = 2/1.

| Catalyst<br>Method of Catalyst Preparation | Example C<br>5% Ru/<br>HZSM-5<br>Impregnation | Example D<br>1% Ru/<br>HZSM-5<br>Impregnation |
|---|---|---|
| Conversion, wt. % | | |
| CO | 82.91 | 79.31 |
| $H_2$ | 88.32 | 84.84 |
| Total Reactor Effluent, wt. % | | |
| Hydrocarbons | 37.54 | 31.83 |
| $H_2$ | 1.46 | 1.92 |
| CO | 14.95 | 18.07 |
| $CO_2$ | 2.31 | 2.66 |
| $H_2O$ | 43.74 | 45.53 |
| Hydrocarbon Composition, wt. % | | |
| $C_1$ | 31.11 | 20.42 |
| $C_2$ | 6.61 | 4.02 |
| $C_3$ | 6.82 | 7.79 |
| $C_4$ | 9.22 | 16.78 |
| $C_5+$ | 46.24 | 50.99 |
| Aromatics in $C_5+$ | 24.84 | 27.04 |
| Aromatics in $C_6+$ | 29.57 | 34.78 |
| Aromatics in Total H.C. | 11.51 | 13.79 |
| Hydrocarbon Selectivity* | 98.50 | 97.60 |
| Octane No. of $C_5+$ | 77 (R + 0)<br>92 (R + 3) | |

*(Total carbon converted - Total carbon in $CO_2$) Total carbon converted.

Having thus generally described the methods and concepts of this invention and discussed specific embodiments and examples in support thereof, it is to be understood that no undue restrictions are to be imposed by reasons thereof except as defined by the following claims.

We claim:

1. In a process for producing a hydrocarbon product effluent by contacting a syngas mixture of hydrogen and carbon monoxide with a catalyst mixture comprising a CO reducing component in combination with a special crystalline zeolite providing a silica to alumina ratio of at least 12 and a constraint index within the range of 1 to 12, the improvement which comprises, converting syngas initially comprising hydrogen and CO in a ratio up to about 2 to 1 to primarily gasoline boiling range hydrocarbons with limited methane production by contacting a catalyst mixture comprising from about 0.2 up to about 5 weight percent of ruthenium in combination with said special crystalline zeolite, maintaining the temperature during contact within the range of about 470° F. to about 650° F. and a pressure within the range of 400 to 1500 psig, selecting a temperature in the range of about 530° to about 650° F. for aromatic gasoline production and in the range of about 470° to about 530° F. for predominantly olefinic gasoline production, separating light gases containing excess carbon monoxide from the reactor product effluent and providing a portion of the separated gases for admixture with fresh syngas feed as required and passed to the syngas conversion step.

2. The process of claim 1 wherein the production of an aromatic containing gasoline is obtained at a temperature within the range of 540 to 620° F.

3. The process of claim 1 wherein the production of an olefinic gasoline is obtained at a temperature within the range of 490° to 530° F.

4. The process of claim 1 wherein the catalyst mixture comprises from about 0.2 up to about 1.5 weight percent of ruthenium.

5. The process of claim 1 wherein the catalyst mixture is brought up to a reaction temperature of at least 450° F. before contact with CO and $H_2$.

* * * * *